US009539847B2

(12) United States Patent
Flynn et al.

(10) Patent No.: US 9,539,847 B2
(45) Date of Patent: Jan. 10, 2017

(54) INDEX LABEL ASSEMBLY

(71) Applicant: Timothy J. Flynn, Key Largo, FL (US)

(72) Inventors: Timothy J. Flynn, Key Largo, FL (US); Geoffrey T. Brossard, Crystal Lake, IL (US)

( * ) Notice: Subject to any disclaimer, the term of this patent is extended or adjusted under 35 U.S.C. 154(b) by 33 days.

(21) Appl. No.: 13/800,442

(22) Filed: Mar. 13, 2013

(65) Prior Publication Data

US 2013/0241189 A1 Sep. 19, 2013

Related U.S. Application Data

(60) Provisional application No. 61/611,665, filed on Mar. 16, 2012.

(51) Int. Cl.

| | |
|---|---|
| ***B42D 15/00*** | (2006.01) |
| ***G09C 3/00*** | (2006.01) |
| ***B29C 51/16*** | (2006.01) |
| ***B60J 10/00*** | (2016.01) |
| ***A61F 13/15*** | (2006.01) |
| ***B32B 9/00*** | (2006.01) |
| ***B32B 33/00*** | (2006.01) |
| ***B65D 65/28*** | (2006.01) |
| ***G09F 3/00*** | (2006.01) |
| ***B42F 21/06*** | (2006.01) |

(52) U.S. Cl.
CPC ............... *B42D 15/00* (2013.01); *B42F 21/06* (2013.01)

(58) Field of Classification Search
CPC ......... B42D 15/00; B42D 25/00; B42D 25/30; G09C 3/00; B42F 21/06
USPC ........ 283/74, 81; 428/40.1, 41.8, 42.2, 42.3, 428/43; 156/212, 221, 226, 227
See application file for complete search history.

(56) References Cited

U.S. PATENT DOCUMENTS

| | | | | |
|---|---|---|---|---|
| 7,857,353 | B2 | 12/2010 | Kuranda et al. | |
| 2008/0093839 | A1 | 4/2008 | Flynn et al. | |
| 2008/0093841 | A1 | 4/2008 | Flynn et al. | |
| 2008/0303265 | A1* | 12/2008 | Kaufman | B42D 15/00 283/81 |
| 2009/0295140 | A1 | 12/2009 | Flynn et al. | |
| 2009/0295143 | A1 | 12/2009 | Flynn et al. | |
| 2010/0102544 | A1 | 4/2010 | Flynn | |
| 2010/0102545 | A1 | 4/2010 | Flynn | |
| 2010/0237604 | A1* | 9/2010 | Flynn | B42D 15/045 283/81 |
| 2011/0186213 | A1 | 8/2011 | Flynn | |

* cited by examiner

*Primary Examiner* — Joseph J Hail
*Assistant Examiner* — Justin V Lewis
(74) *Attorney, Agent, or Firm* — Pauley Erickson & Kottis

(57) ABSTRACT

An index label and a method for applying an index label to a sheet or folder. A label assembly includes labels in a column, and each of the labels includes a fold line. A registration structure is adjacent the label column. Each label can be partially folded into a raised position, and the item to be label placed adjacent the raided portions, such as using the registration structure to align the item. The raised portion is lowered and adhered to the item. The remainder of the label is then removed from the label assembly and folded to adhere to itself and/or the item to form an index label on the item.

18 Claims, 7 Drawing Sheets

INDEX LABEL ASSEMBLY

CROSS REFERENCE TO RELATED APPLICATION

This application claims the benefit of U.S. Provisional Patent Application Ser. No. 61/611,665, filed on 16 Mar. 2012. The Provisional Application is hereby incorporated by reference herein in its entirety and is made a part hereof, including but not limited to those portions which specifically appear hereinafter.

FIELD OF THE INVENTION

This invention is directed to an index label that can be adhered to a page, sheet, or folder, and that extends past an edge of the page, sheet, or folder. The invention is also directed to a printable sheet of such labels, and a method for applying the printed labels, such as by a consumer, to form an index label.

BACKGROUND OF THE INVENTION

Printable index labels are known, for example, in U.S. Pat. No. 7,857,353, herein incorporated by reference. The labels are removed and folded to form an index label adhered to a sheet or folder. The placement and alignment of the index labels on the object to be labeled is handled by the consumer user, and although the folded label can provide lines or reference edges for alignment, off-centered adhesion may still occur.

SUMMARY OF THE INVENTION

This invention includes a printable sheet of removable index labels that incorporates a registration structure to assist in aligning the object to be labeled (paper, folder, etc.) with the label. The registration structure is desirably integrated with the label sheet, such as a part of the label and/or on opposing sides of the label, to register or align the object against the label.

An object of the invention can be attained, at least in part, through a label assembly. The label assembly includes a face sheet, a back sheet, and a layer of adhesive disposed between the face sheet and the back sheet. The adhesive adheres to the face sheet more than to the back sheet. At least one and desirably a plurality of label shapes is cut within a remaining portion of the face sheet. The label shapes can include at least a first label column. At least one fold line extends across the label shapes in the first label column. The fold line can be a printed line, a score line, a perforated line, and combinations thereof. Desirably, the fold line divides each of the label shapes into a first portion and a second portion, where the first portion is larger than the second portion.

A registration structure is aligned with the label or the label column. The registration structure is one of raised or raisable above the face sheet, to allow the object to be labeled to be positioned against the registration structure for proper alignment with the label. The registration structure can be formed in or by the label, the face sheet, and/or both the face sheet and the back sheet, depending on need. In one embodiment of this invention, the registration structure is a raisable portion of the label itself, such as foldable about a fold line. In another embodiment, the registration structure is, or includes an additional structure, such as a raisable tab, formed in the remaining portion or matrix of the face sheet surrounding the label(s).

The invention further comprehends a method of using the label assembly of this invention. The method includes writing or printing on one or more labels, such as by feeding the label assembly through a printer operatively connected to a computer. The method further includes folding a portion of one of the labels to an upwardly extended position relative to or above the face sheet. In embodiments including alternative or additional registration structure beyond the folded label portion, the method includes folding the further registration structure(s) to an upwardly extended position relative to or above the face sheet. With the label assembly on a flat surface, the object to be labeled, such as a sheet or folder, is placed against the raised label portion and/or registration structure to align the object with the label. With the object aligned against the raised label portion and/or registration structure, the folded portion of the label is adhered, such as by lowering onto, the object.

The invention still further comprehends a label assembly. The label assembly includes a face sheet, a back sheet, and a layer of adhesive disposed between the face sheet and the back sheet. The adhesive adheres to the face sheet more than to the back sheet. A plurality of label shapes is cut within a remaining portion of the face sheet. The label shapes including at least a first label column and a second label column. Two parallel fold lines extend across the label shapes of each of the first label column and the second label column. A first registration structure is disposed aligned with the first label column and a second registration structure is disposed aligned with the second label column. The first and second label columns and the fold lines are arranged lengthwise on the label assembly.

The registration structure of this invention can comprise a registration tab formed as a foldable portion of the label and/or separately cut within at least the face sheet. Preferably, the registration structure for each label or label column includes a registration tab on at least one side, and desirably each of opposing sides of the label or label column, and aligned with the label or label column. When the registration tab is lifted above the face sheet, the tab provides a stop for a point on the object. By placing the object against the raised tabs, the object is properly aligned with the label and reduces or eliminates crooked label application.

BRIEF DESCRIPTION OF THE DRAWINGS

These and other objects and features of this invention will be better understood from the following description taken in conjunction with the drawings.

DESCRIPTION OF THE DRAWINGS

Figure 1:
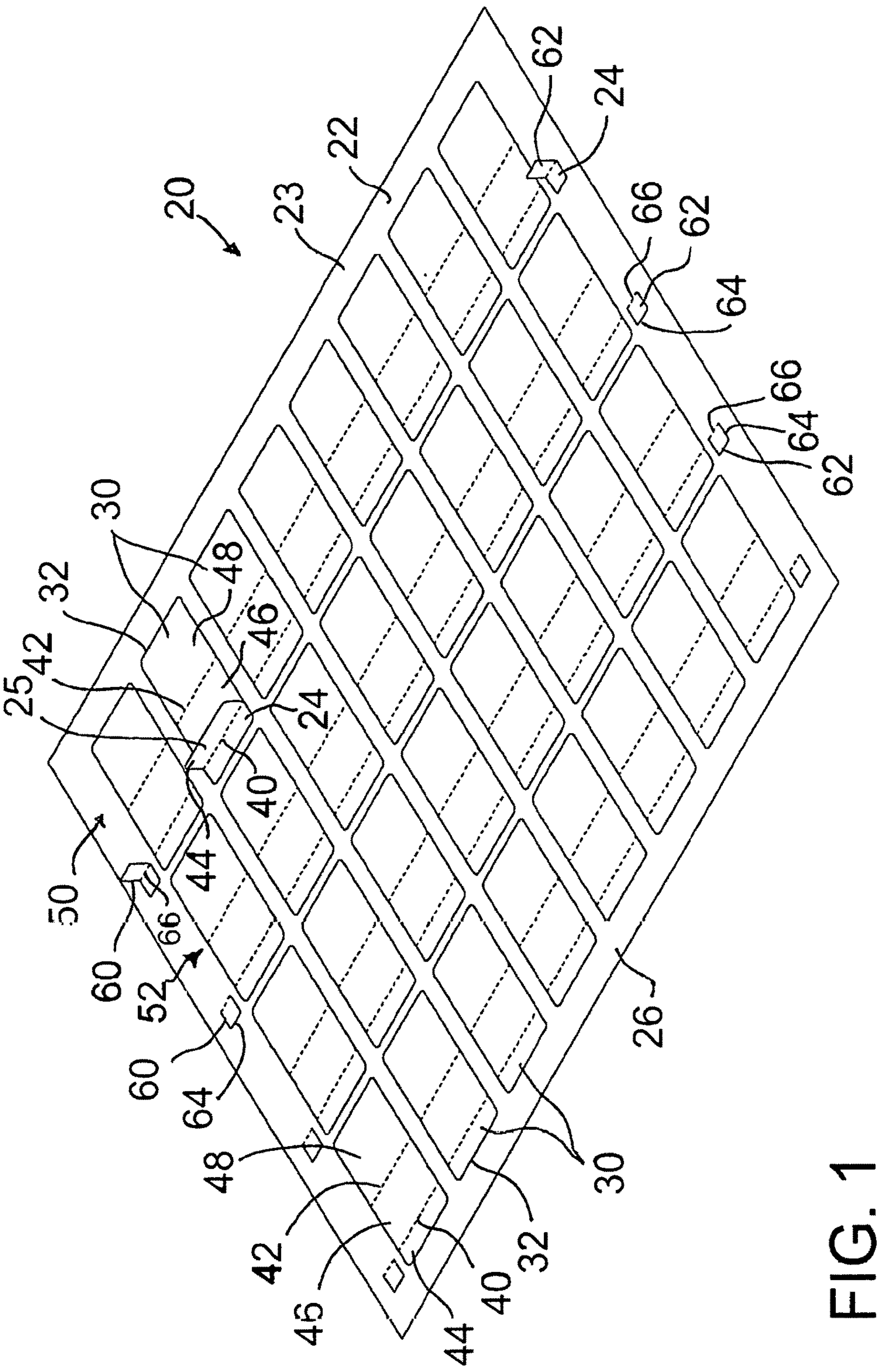
FIGS. 1-6 illustrate a label assembly and its use in labeling an object according to one embodiment of this invention.

FIG. 1 illustrates a label assembly 20 (not necessarily shown to scale) according to one embodiment of this invention. Label assembly 20 is desirably formed of a face sheet 22 and a back sheet 24. The back sheet is desirably about the same size as the face sheet 22, but may be slightly larger or smaller than the face sheet 22. The surface of the face sheet 22 that is disposed toward the back sheet 24 includes an adhesive coating 25. The adhesive coating can include any adhesive material known and available to those skilled in the art for forming pressure sensitive, or self-adhesive labels. The back sheet 24 is desirably formed of a material to which the adhesive coating adheres significantly less than to the face sheet 22, such as is known for forming pressure sensitive, or self-adhesive labels.

The sheet 20 is of any suitable shape, and generally any suitable size that can be accepted by and fed through a printer, such as a laser printer or an ink jet printer. Common sizes of paper generally fed through printers are 8.5 inches by 5.5 inches, 8.5 inches by 11 inches, 8.263 inches by 11.688 inches (A4 size), and 8.5 inches by 14 inches. The face sheet 22 is preferably, but not necessarily, constructed of any suitable paper, paper composite, non-metal and/or metal material that can be used as a label. Other suitable materials for constructing the sheet 22 include fabric, plastic, and metal foils. The adhesive coating covered by the back sheet is applied to the face sheet 22 in any suitable manner known to those skilled in the art. The face sheet 22 desirably has a printable surface 23 on a side opposite the adhesive coating.

The face sheet 22 and the printable surface 23 can be any of a variety of face materials used to make pressure sensitive, or self-adhesive labels. Such face materials may include, but are not limited to: smudgeproof stock, litho stock, cast coated stock, tag stock, fluorescent stock, foils, computer printable polyester, vinyl, satin cloth, Tyvek™ material, flexible plastic, book papers, photo quality papers and/or photo quality film. Furthermore, various portions of the face materials can be different colors, thereby resulting in different colored parts.

The phrase "printable surface" relates to a surface of any type of matter upon which a consumer or consumer machine can draw, print, color, paint, photocopy, write, emboss, or make any other type of mark or graphic. Laser printers, ink jet printers, impact printers, thermal transfer printers, direct thermal printers, typewriters, or any other suitable graphic printing devices are preferred but not necessary for use with printable surfaces according to this invention.

The face sheet 22 includes a plurality of shapes 30, each defining an individual label according to this invention. The phrase "shape", or the phrase "removable shape" or "tearable shape", is intended to relate to a shape, such as the shapes identified in FIG. 1 by element reference numerals 30, that can be torn away from a remaining portion 26 of the sheet 22, by using tearable lines of separation 32, such as die-cut lines, perforated lines, micro-perforated lines, or any combination of these types of separation, or any other suitable structure that enables separation. A preferred type of tearable line 32 is a line that is die-cut. The label shapes 30 can be die-cut along at least a portion of a periphery, such that the label shapes 30 can be easily removed or separated from the remaining portion 26 of the sheet 22, for example after the sheet 22 is run through a printer.

Each label shape 30 of FIG. 1 includes two fold lines 40 and 42. The fold lines 40 and 42 extend parallel and spaced apart across each of the label shapes 30. The fold lines 40 and 42 divide each of the label shapes 30 into three portions, a first portion 44, a second portion 46, and a third portion 48. Desirably, the first portion 44 is sized smaller than the second portion 46, which is sized smaller than the third portion 48. In one embodiment the second fold line 42 is disposed across the midpoint of the label shape 30, so that the third portion 48 is equal to the first portion 44 plus the second portion 46. The fold lines 40 and 42 can be embodied in various and alternative ways, such as are known by those skilled in the art. In the embodiment shown in FIG. 1, the fold lines 40 and 42 include a score line or a perforated line, alone or in combination with a printed line, that desirably facilitates folding along the fold lines 40 and 42.

The label assembly 20 shown in FIG. 1 includes a first column 50 of label shapes 30 and a second column 52 of label shapes 30. Each of the first and second label columns is arranged or stacked lengthwise on the label assembly 20. The label assembly 20 can also include an optional separation line (not shown) dividing the label assembly into two or more sets of label shapes 30. The optional separation line allows the label assembly 20 to be separated in two by the user, if desired depending on need, either before of after printing on the printable surface 23. In one embodiment of this invention, the separation line is formed by a first tearable line of separation extending across the face sheet and a second tearable line of separation extending across the back sheet. The separation line is desirably formed by a perforated line of separation including a plurality of cuts and ties.

The label sheet 20 includes a registration structure, embodied in FIG. 1 as including the foldable label portion 44 and/or pairs of spaced apart tabs 60 and 62. Each of the tabs 60 and 62 is, disposed on an opposing side relative to each label shape 30. In the particular embodiment of FIG. 1, the tabs 60 and 62 are disposed on opposing sides of each label column to function for each label 30 in the corresponding label column. As will be described in more detail below, the registration structure of this invention allows for improved and easier application of the index label to an object. In the embodiment of FIG. 1, the tabs 60 and 62 are each defined on three sides by a tearable line of separation 64 in at least the face sheet 22, and optionally both the back sheet and the face sheet 22. The tabs 60 and 62 are raisable to an extended position by folding about a registration fold line 66 outward above the face sheet 22 as shown in FIG. 1. The registration fold line 66 is aligned with and parallel to one of the fold line 42 of the labels. Alternatively, such as in an embodiment where the label shape 30 has one fold line, the registration fold lines are aligned with a portion of the label where the object to be labeled is to be placed for labeling, such as shown in the upper column FIG. 7.

The invention includes a method for labeling an object, such as a sheet or folder with an indexing label. The label shape includes a raisable portion that is raised for application. The object to be labeled is placed adjacent the registration structure to align the object for labeling. The registration structure can be the raised label portion itself, markings on the label assembly, and/or raisable tabs, as discussed above. Once aligned, the raised portion of the label is lowered onto, and adhered to, the object. The object can be lifted to remove the remainder of the label sheet, and the label can be further wrapped around the object, via a fold line in the label, to adhere the label to itself and/or the object, such as on an opposite side of the object.

Figure 2:
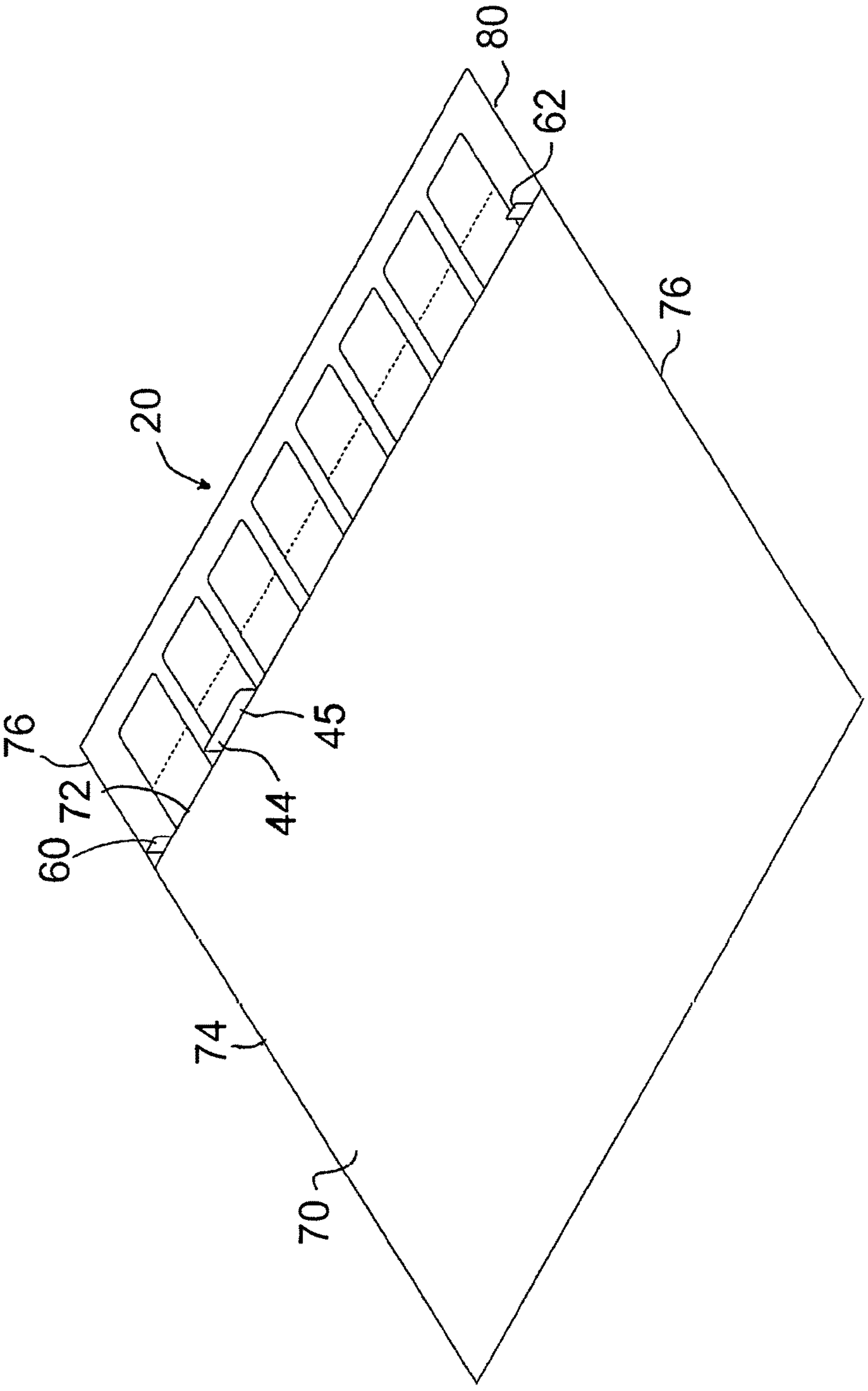

FIGS. 2-6 illustrate the operation of the label sheet 20 of FIG. 1 for labeling an object, shown as sheet 70. Desirably first, if needed or desired, the label sheet 20 is routed through a consumer printer to print consumer-created text and/or graphics onto the printable surface 23 of at least one label shape 30. In FIG. 1, the label assembly is prepared for application of one of the labels 30 by raising the first portion 44 about fold line 40, and also by raising the tabs 60 and 62 about corresponding fold lines 66. FIG. 2 shows a sheet 70, which can be a plain paper or cardstock sheet or a file folder, placed against the first portion 44 and the tabs 60 and 62. As discussed above, the tabs 60 and 62 can be optionally formed by one or more die cuts that extend through both of the back sheet 24 and the face sheet 22, thereby providing increased tab thickness and thus rigidity for receiving the sheet 70 there against. The tabs 60 and 62 desirably assist the user in positioning the sheet 70 in proper alignment with the portion 44 of label shape 30 to promote or provide a desirable straight label application.

In an alternative embodiment without tabs 60 and 62, the edge 72 of sheet 70 can be aligned against the folded portion 44 of the label 30 as a registration structure or registration tab. Including one additional registration tab 60 or 62 in the matrix 26 provides assistance in aligning the sheet 70 straight with respect to the folded portion 44. In the particular embodiment shown in FIG. 2, the placement of the sheet 70 against the tabs 60 and 62 on opposing sides of the folded label 30 provides for additional assistance in keeping the sheet 70 aligned straight relative to the folded portion 44.

Figure 3:
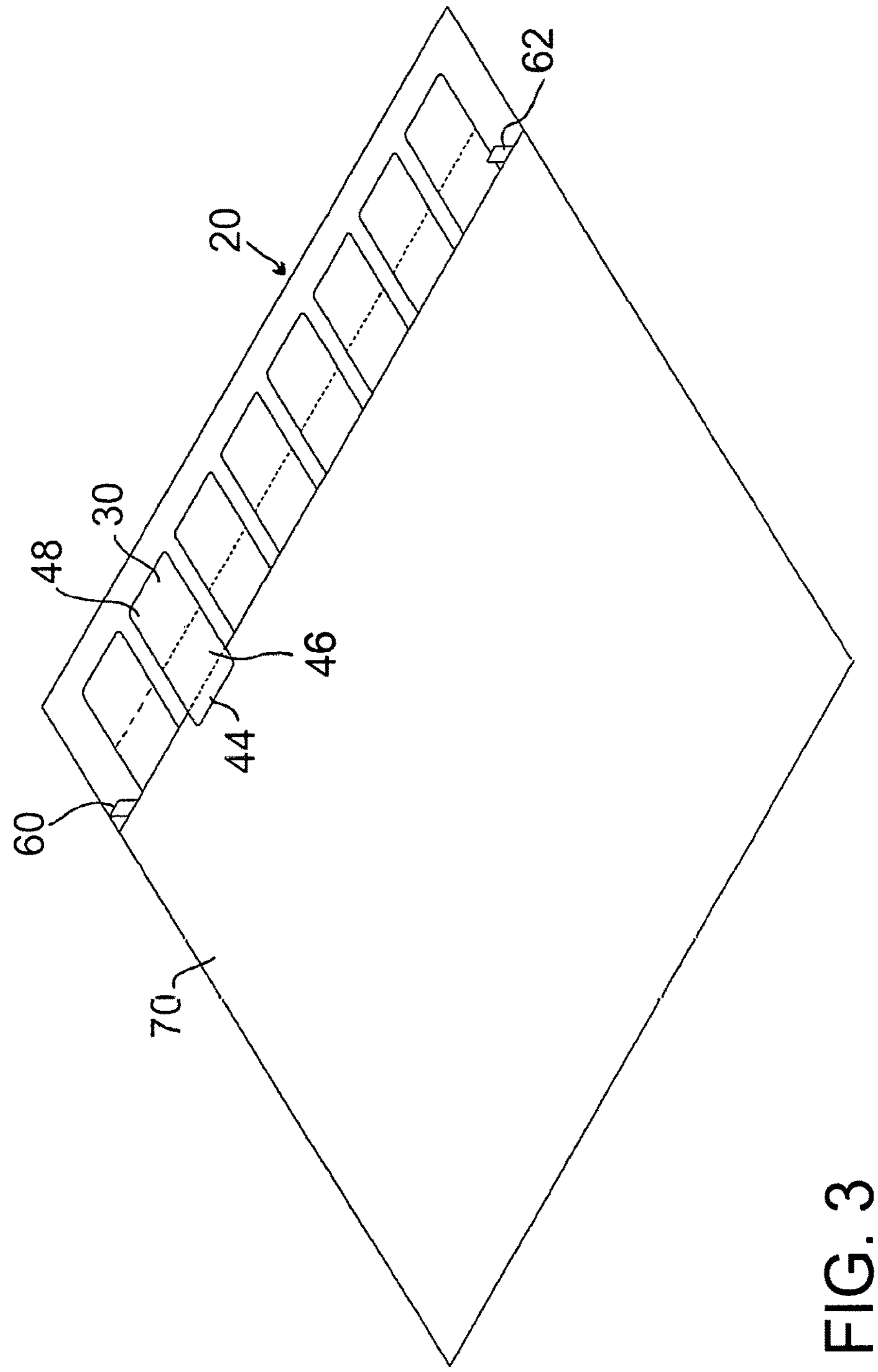
Figure 4:
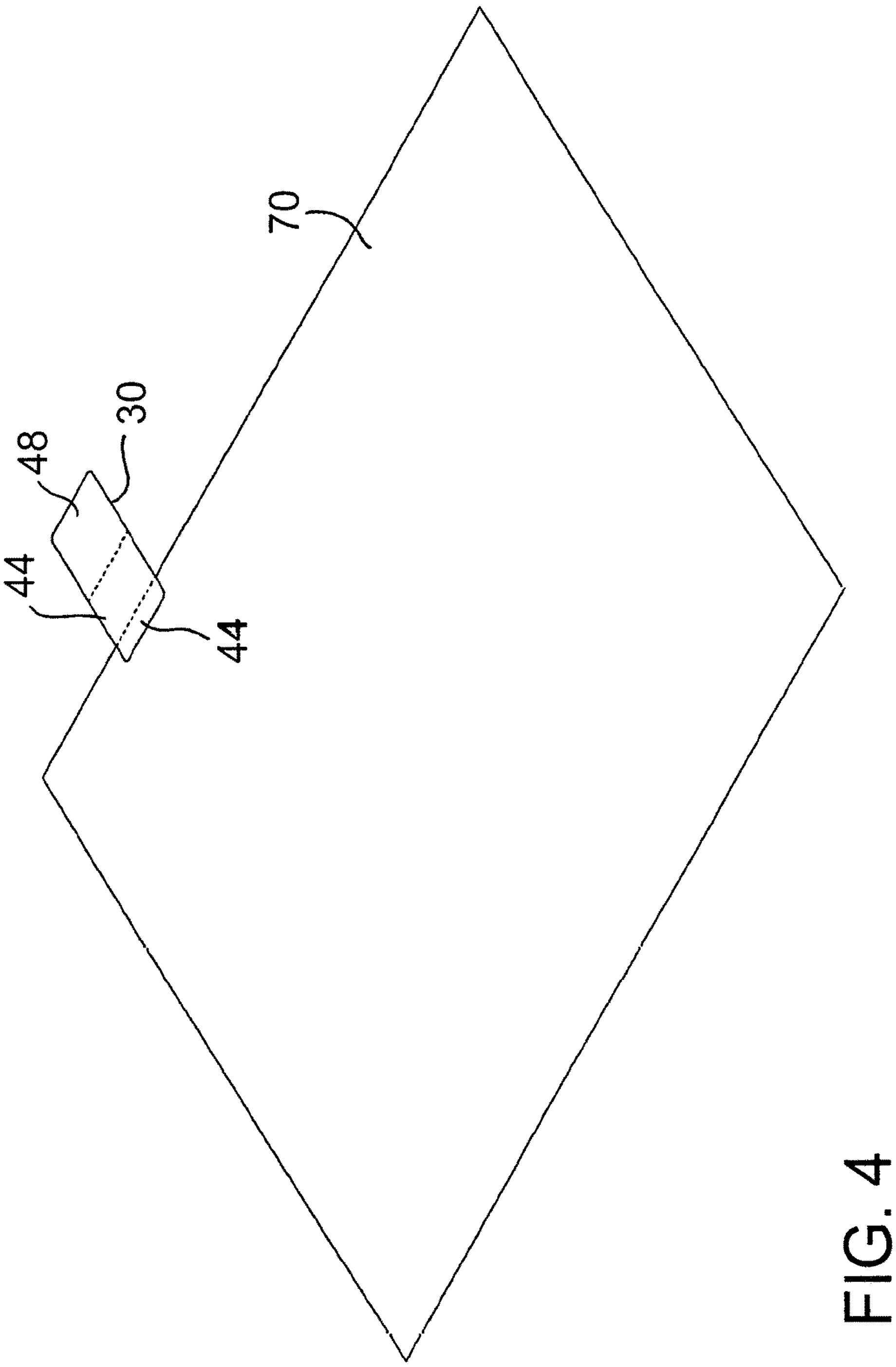
Figure 5:
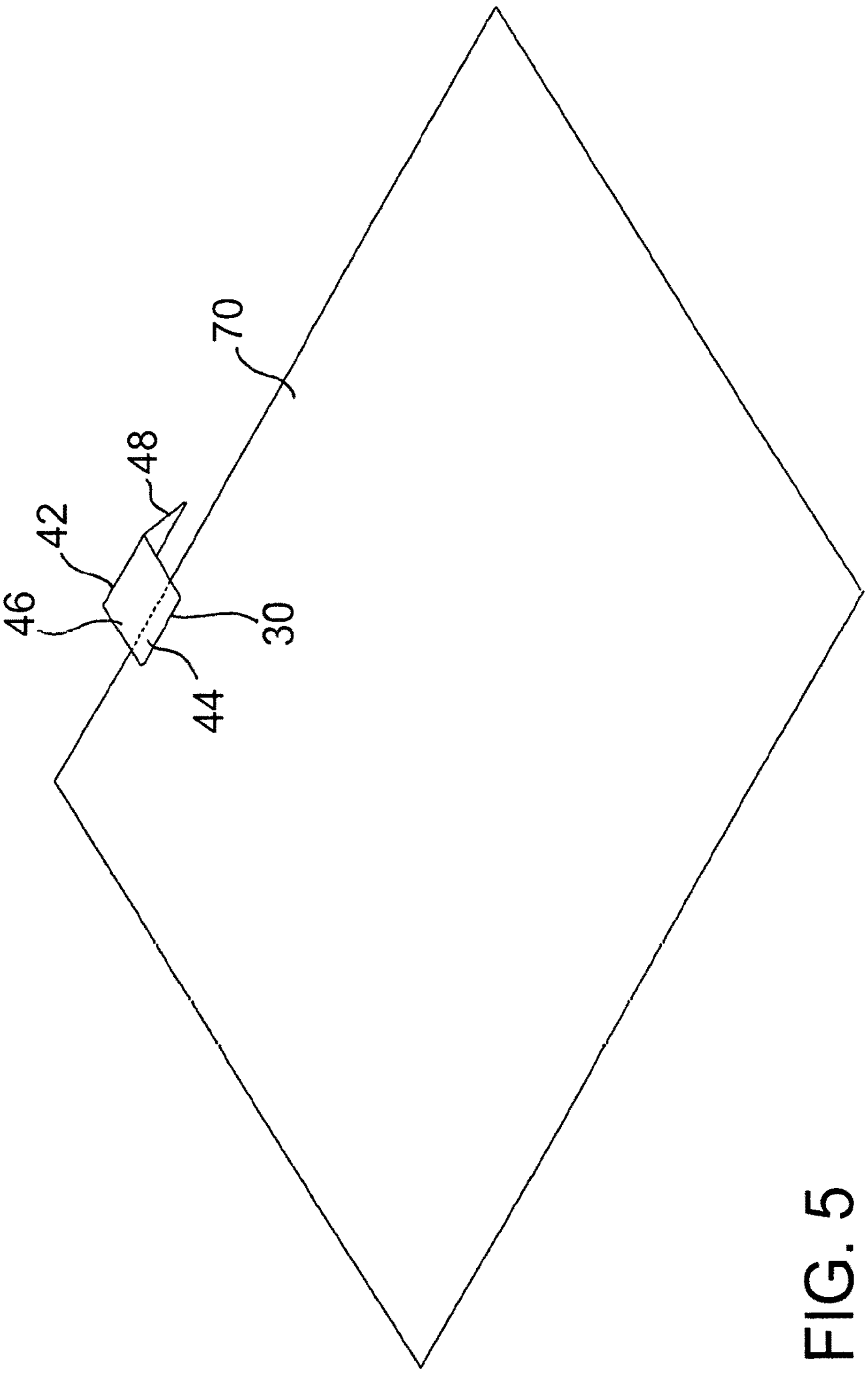

To apply the first portion 44 of label shape 30 to the sheet 70, the first portion 44 is pressed down so that surface 45 is adhered on the sheet 70 while the sheet 70 remains in contact with tabs 50 and 52. The resulting position is shown in FIG. 3, with portions 46 and 48 of label 30 still adhered to the back sheet of the label assembly 20. The sheet 70 is lifted with the adhered label 30 to remove the label 30 from the label assembly 20, as shown in FIG. 4. In FIG. 5, the third portion 48 of label 30 is folded about fold line 42 to adhere the third portion 48 to the adhesive side of second portion 46 and sheet 70.

Figure 6:
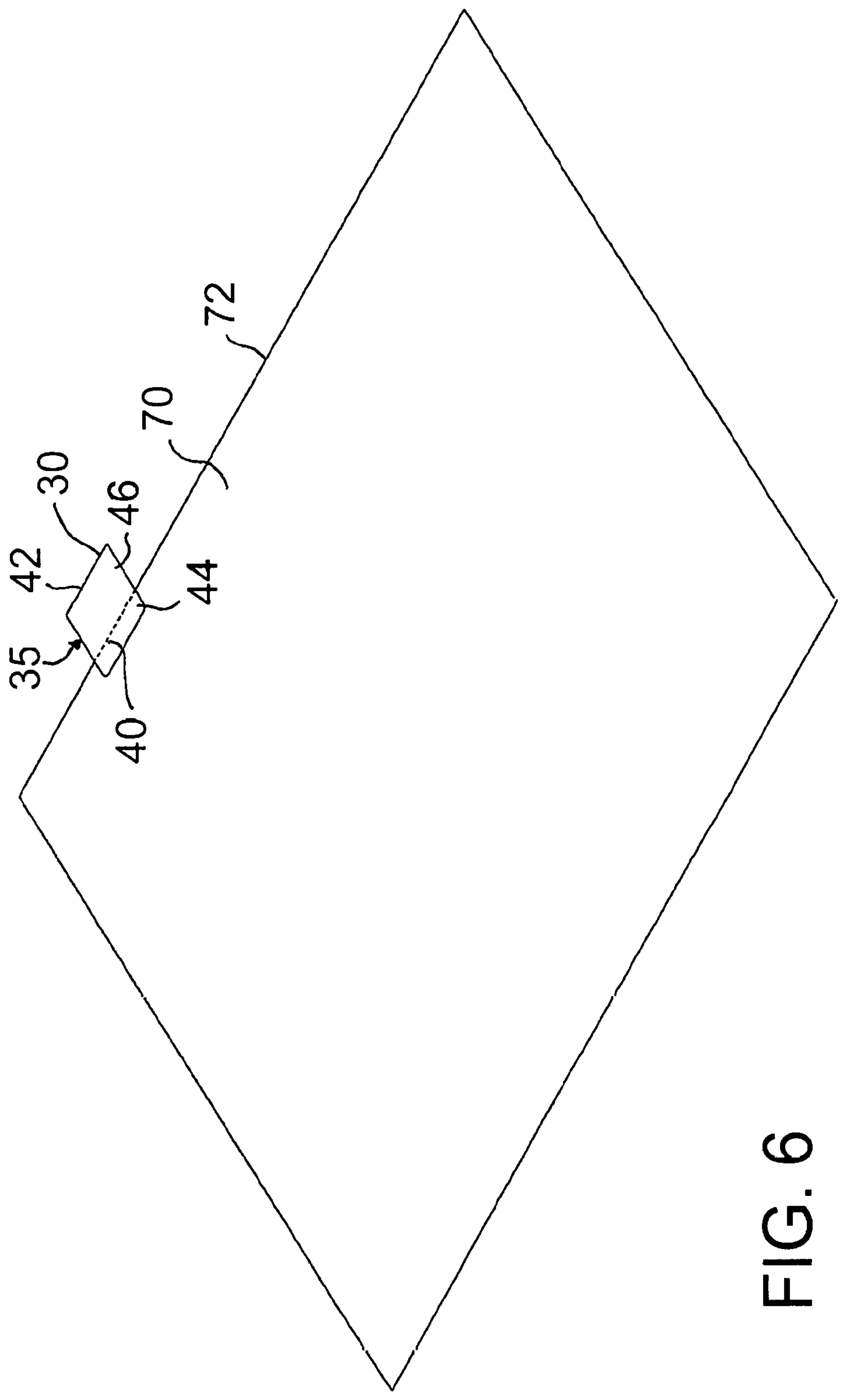

FIG. 6 illustrates a removed and folded label shape 30 attached to the sheet 70 as an index label 30, according to one preferred embodiment of this invention. The third portion 48 of the label 30 is folded about fold line 42, such that the adhesive coated side of the second portion 46 is adhered to and covers a portion of the adhesive coated side of the second portion 46 of the label 30. The remaining part of the adhesive side of the label third portion 48 (i.e., that which is not adhered to the label second portion 46) is adhered to the sheet 70. The label 30 is attached to the sheet 70 such that a tab portion 35 of the label 30 extends beyond the edge 72 of the sheet 70. The tab portion 35 is formed by the label third portion 48 folded back over the second portion 46. The formed tab portion 35 thus includes two printable surfaces (at least one of which is typically printed on, if desired), one on either side of the tab portion 35. The tab portion 35 desirably does not include any exposed adhesive material.

Repeating the steps for each label 30 in column 50 provides a plurality of sheets with index labels. By aligning the top and bottom edges 74 and 76 of each sheet 70 with the corresponding top and bottom edges 78 and 80 of the label assembly 20, the index labels 30 can be applied in staggered positions that are useful for indexing the sheets.

As will be appreciated by those skilled in the art following the teachings herein provided, various and alternative sizes, shapes, and configurations are available for the label assembly, label columns, label shapes, label portions, and registration structures and tabs of this invention. For example, the length and/or width of the index labels can vary, depending on need. As a further example, in one embodiment of this invention, the second portion of the label shape of this invention, which is the portion intended to extend beyond the page the label is adhered to, can include matching a fanciful shape, such as a star or circle, for which the third portion of the label shape includes a matching shape with an additional extension portion matching the first portion, for adhering to the sheet.

Figure 7:
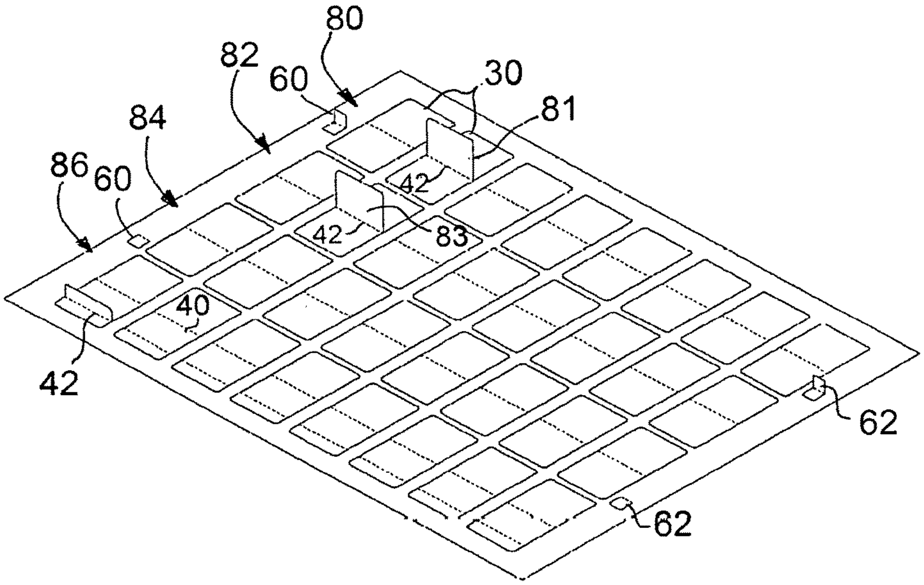
FIG. 7 illustrates alternative embodiments and/or positions of the registration structure of this invention.

FIG. 7 illustrates a label assembly having four label columns, each including an alternative registration structure according to this embodiment. Each of the alternative registration structure is suitable for use with all labels of a label assembly. Label column 80 includes a registration structure including two tabs 60 and 62, each aligned at a point of the label 30 between the fold line 42 and the label end, and not aligned with the fold line 42 forming label portion 81. Label column 82 includes only the foldable or raisable portion 83, foldable about fold line 42. The registration structure of label column 84 includes tabs 60 and 62 positioned similar to FIG. 1, but without the further fold line 40 of FIG. 1. The registration structure of label column 86 includes two fold lines 40 and 42, and no tabs in the remaining portion. Additional suitable registration structure and/or tab embodiments are disclosed in U.S. Patent Application Publications 2008/0093839; 2008/0093841; 2009/0295143; 2009/0295140; 2010/0102544; 2010/0102545; and 2011/0186213, each herein incorporated by reference.

Thus, the invention provides an index label and a consumer-printable sheet of shapes for forming user-printed labels that can be folded into and used as index labels. The apparatus and method of this invention can also be incorporated into an automatic or manual label application machine.

It will be appreciated that details of the foregoing embodiment, given for purposes of illustration, is not to be construed as limiting the scope of this invention. Although only a few exemplary embodiments of this invention has been described in detail above, those skilled in the art will readily appreciate that many modifications are possible in the exemplary embodiments without materially departing from the novel teachings and advantages of this invention. Accordingly, all such modifications are intended to be included within the scope of this invention. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

What is claimed is:

1. A label assembly, comprising:

a face sheet, a back sheet, and a layer of adhesive disposed between the face sheet and the back sheet, the adhesive adhering to the face sheet more than to the back sheet;

a label column extending across the face sheet between a first column end and an opposing second column end, the label column including a plurality of label shapes cut within a remaining portion of the face sheet between the first column end and the second column end;

a fold line extending across each of the label shapes in the label column, the fold line disposed perpendicular to the first column end and the second column end; and a registration structure aligned with the label column, the registration structure comprising two raisable tabs, a first of the tabs disposed in the remaining portion beyond the first column end and a second of the tabs disposed in the remaining portion beyond the opposite second column end, each of the tabs defined by a tearable line of separation and connected to the remaining portion by a registration fold line that is parallel to the fold line of the each of the label shapes in the label column, wherein the registration fold line of each of the tabs is collinearly aligned with the fold line of each of the label shapes in the label column.

2. The label assembly of claim 1, wherein each of the fold line and the registration fold line comprises a score line, a perforated line, or combinations thereof.

3. The label assembly of claim 1, wherein the label assembly is approximately 8.5 inches by 11 inches or approximately A4 sized, and each of the label shapes is an indexing label.

4. The label assembly of claim 1, wherein the label column is arranged lengthwise on the label assembly.

5. The label assembly of claim 1, further comprising a second plurality of label shapes arranged in a second label column, and a second fold line extending across each of the second plurality of label shapes.

6. The label assembly of claim 1, further comprising two fold lines extending across each of the label shapes in the label column.

7. The label assembly of claim 6, wherein one of the two fold lines divides each of the label shapes into approximately equal portions.

8. The label assembly of claim 6, wherein the two fold lines divide each of the label shapes into three portions, wherein a first portion is sized smaller than a second portion, and the second portion is sized smaller than a third portion.

9. The label assembly of claim 8, wherein one of the fold lines is disposed across a midpoint of each of the label shape, wherein the third portion is sized equal to the first portion plus the second portion.

10. A method of using the label assembly of claim 1, the method comprising:
- feeding the label assembly through a printer operatively connected to a computer;
- printing on the face sheet within the plurality of label shapes;
- folding one of the label shapes about the fold lines to raise a first portion of the label shape off the back sheet;
- folding at least one raisable tab of the two raisable tabs about the registration fold line to raise the at least one raisable tab off the back sheet;
- aligning an object against the raised first portion and the at least one raisable tab;
- lowering the first portion onto the object and adhering the first portion to the object;
- removing a remainder of the label shape from the label assembly; and
- folding the label shape about the fold line to adhere a second portion of the label shape to at least one of itself or the object.

11. The label assembly of claim 1, wherein the registration fold line of each of the tabs is in line with the fold line of each of the label shapes in the label column.

12. The label assembly of claim 1, wherein the registration fold line of each of the tabs is within a same axis as the fold line of each of the label shapes in the label column.

13. The label assembly of claim 1, wherein an end of the registration fold line of each of the tabs is adjacently aligned facing an end of the fold line of one of the label shapes in the label column.

14. A label assembly, comprising:
- a face sheet, a back sheet, and a layer of adhesive disposed between the face sheet and the back sheet, the adhesive adhering to the face sheet more than to the back sheet;
- a label shape cut within a remaining portion of the face sheet, the label shape including a fold line extending across the label shape and defining a first portion of the label; and
- a registration structure disposed in the remaining portion, the registration structure connected to the remaining portion by a registration fold line that is collinearly aligned parallel to and with the same axis as the fold line of the label shape, and the registration structure aligned adjacent to the first portion of the label shape whereby folding about the registration fold line raises the registration structure off the back sheet and folding about the fold line raises the first portion of the label off the back sheet and into a position aligned and in a same vertical plane with the registration structure.

15. The label assembly of claim 14, wherein the registration structure comprises a tab cut in the remaining portion.

16. The label assembly of claim 14, wherein the registration structure comprises two tabs cut in the remaining portion and disposed on opposing sides of the label shape, and each of the tabs including the registration fold line disposed parallel with the fold line of the label shape.

17. The label assembly of claim 16, further comprising a second fold line parallel to the fold line and extending across a midpoint of the label shape.

18. A method of using the label assembly of claim 14, the method comprising:
- feeding the label assembly through a printer operatively connected to a computer;
- printing on the face sheet within the plurality of label shapes;
- folding the label shape about the fold line to raise a portion of the label shape off the back sheet;
- folding the registration structure about the registration fold line to raise the registration structure;
- aligning an object against the registration structure and the portion of the label shape;
- adhering the raised first portion to the aligned object;
- removing a remainder of the at least one label shape from the label assembly; and
- folding the label shape about the fold line to adhere the label shape to at least one of itself or the object.

* * * * *